United States Patent [19]

Newman et al.

[11] Patent Number: 5,396,905
[45] Date of Patent: Mar. 14, 1995

[54] SURGICAL DRAPE WITH INTEGRAL MRI COIL

[75] Inventors: Robert Newman, Milwaukee; Ralph S. Hashoian, Brookfield, both of Wis.

[73] Assignee: General Electric Company, Milwaukee, Wis.

[21] Appl. No.: 219,579

[22] Filed: Mar. 29, 1994

[51] Int. Cl.⁶ .................... A61B 19/00; A61B 19/08; G01R 33/20
[52] U.S. Cl. .................... 128/849; 128/853; 324/318
[58] Field of Search ............... 128/849–856; 324/18; 606/32

[56] References Cited

U.S. PATENT DOCUMENTS

| | | | |
|---|---|---|---|
| 3,667,458 | 6/1972 | Krebs | 128/853 |
| 4,594,566 | 6/1986 | Maudsley | 324/318 |
| 4,634,980 | 1/1987 | Misic | 324/318 |
| 4,703,272 | 10/1987 | Arakawa | 324/318 |
| 4,712,067 | 12/1987 | Roschmann | 324/318 |
| 4,791,371 | 12/1988 | Krol | 324/318 |
| 4,891,596 | 1/1990 | Mitomi | 324/318 |
| 5,042,981 | 8/1991 | Gross | 606/32 |

*Primary Examiner*—Michael A. Brown
*Attorney, Agent, or Firm*—Quarles & Brady

[57] ABSTRACT

A radio frequency coil for an magnetic resonance imaging system is integrated into a disposable surgical drape to permit imaging during a surgical procedure. The drape is formed by two sheets of flexible material with an adhesive applied to an exposed surface for adhering the drape to skin of a patient. A flexible radio frequency coil, tuned to the Larmor frequency, is sealed between the two sheets and surrounds an area of the drape through which an incision is made during surgery on the patient. A layer of material that is resistant to penetration by surgical instruments covers and protects the radio frequency coil during surgery.

9 Claims, 1 Drawing Sheet

SURGICAL DRAPE WITH INTEGRAL MRI COIL

BACKGROUND OF THE INVENTION

This invention relates to magnetic resonance imaging, and more particularly to local coils for imaging specific anatomical features of a patient.

Magnetic resonance imaging is a common modality used to image different portions of a patient's anatomy. In doing so, the patient is placed in a strong uniform magnetic field to polarize nuclei within the cells of the patient causing the nuclei to precess at their characteristic Larmor frequency. By applying another excitation magnetic field near the larmor frequency, the precessing nuclei become aligned. The signals emitted at the Larmor frequency by the precessing nuclei when the excitation field is removed are detected and employed to create an image of the internal anatomy of the patient.

The basic magnetic resonance imaging system utilizes coils which enclose substantially the entire body of the patient and excite the nuclei within that portion. When only a specific section of the patient's body is desired to be imaged, a smaller radio frequency coil often is used to excite the nuclei and to receive the signals emitted by the nuclei thereafter. Such smaller coils are often referred to as local coils, and a variety of them have been designed specifically to image the spine, abdomen, extremities and other body regions.

Although most of the MRI imaging was performed for diagnostic purposes, it is desirable to be able to perform magnetic resonance imaging during surgical procedures. During such procedures, a detailed image of the region of exploration is created using the magnetic resonance system to guide the manipulation of instruments by the surgeon. However, the structure of conventional coils made it impractical to cut holes through the coil to gain access to the patient's anatomy. In addition, the introduction of other equipment into a full body coil can interfere with the excitation of the nuclei and the reception of their emitted signals. Heretofore, the local coils designed for specific parts of the patient's anatomy were rigid structures and did not permit access to that portion by surgical instruments.

SUMMARY OF THE INVENTION

An object of the present invention is to incorporate a local radio frequency coil into a surgical drape to permit magnetic resonance imaging to occur during a surgical procedure.

To satisfy that objective, a surgical drape includes a sheet of sterile flexible material having a mechanism, such as an adhesive applied to one surface, for adhering the sheet to skin of a patient's body. A flexible radio frequency coil is attached to the sheet and surrounds an area through which an incision is made through the sheet and the underlying skin during the surgical procedure. The flexible radio frequency coil is designed to match the size and conform to the contour of the corresponding part of the patient's body, and is tuned to the Larmor frequency of magnetic resonance.

In the preferred embodiment of the present invention the sheet is formed by two layers bonding together with the radio frequency coil sealed between the two layers. It is also desirable to protect the radio frequency coil by covering it with a sheet of material that is resistant to penetration by surgical instruments.

DESCRIPTION OF THE PREFERRED EMBODIMENT

Figure 1:
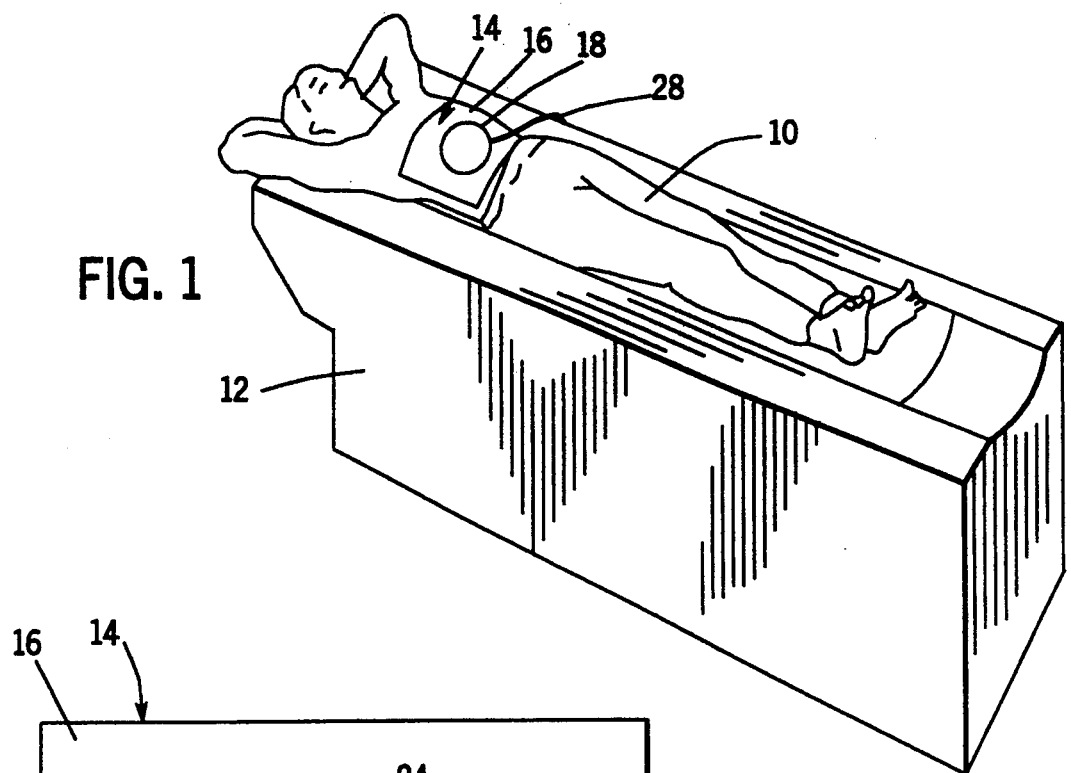
FIG. 1 is an isometric view of a patient lying on a table of an MRI system.

FIG. 1 illustrates a patient 10 lying on a table 12 which is within the magnetic polarizing field of a magnetic resonance imaging system. In this case, the patient has been prepared for abdominal surgery and a surgical drape 14 according to the present invention has been placed over that portion of the patient's anatomy. The drape comprises a plastic transparent sheet 16 having an MRI radio frequency (RF) coil 18 attached thereto. The surgical drape 14 provides a sterile protective covering over the patient's skin. In addition, the adhesive attachment of the drape fixes the position of the RF coil 18 with respect to the anatomical features being imaged.

Figure 2:
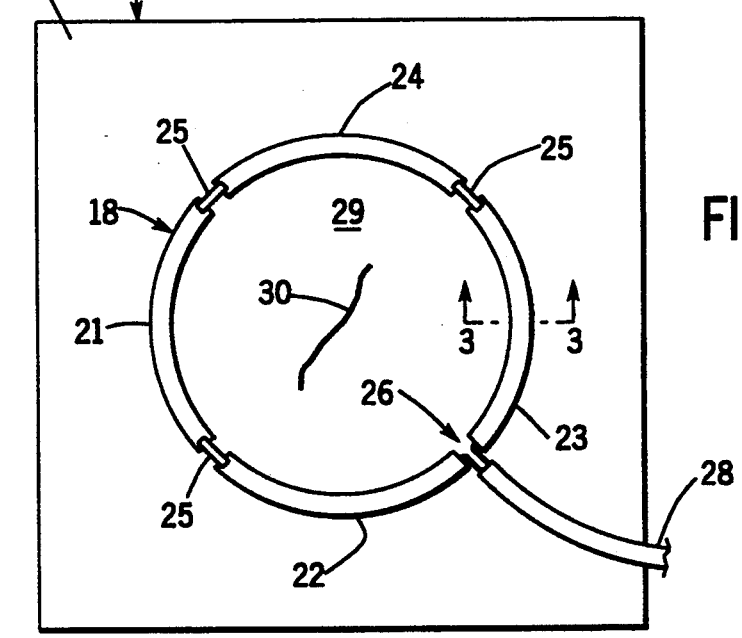
FIG. 2 is a plane view of a surgical drape according to the preset invention.
Figure 3:
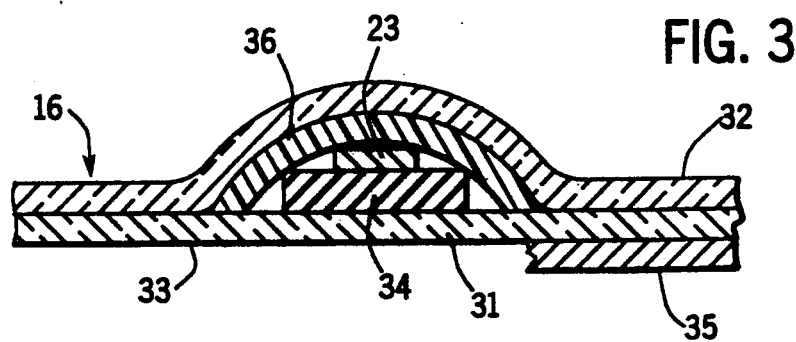
FIG. 3 is an enlarged cross-section view taken along line 3—3 in FIG. 2.

The drape 14 is shown in greater detail in FIG. 2 and 3 comprises a square sheet 16 formed of a transparent plastic. Although a transparent sheet is preferred, opaque or translucent material may be used and other materials than plastic, such as paper for example, can be employed. The underside surface 33 of the sheet 16 is coated with an adhesive which allows the drape to adhere to the skin of the patient covering the region in which the incision will be made. For example, the surface 33 may have an adhesive applied to it with a paper backing sheet 35 (FIG. 3) with a wax coating attached over the adhesive. The backing paper sheet 35 is peeled away prior to use and the adhesive remains of the surface 33. Although a square sheet 16 is shown, the sheet may take on a rectangular, oval or other geometric shape as may be desirable to conform to the skin of the patient over the operating region.

In the illustrated embodiment, the RF coil 18 has a circular shape formed by a number of arcuate segments 21, 22, 23 and 24 of approximately ninety degrees and lying in a circle with gaps between ends of adjacent segments. Tuning capacitors 25 are connected between adjacent segments across three of the gaps. The capacitors 25 tune the coil 18 for the Larmor frequency of interest. A coaxial cable 28 has a pair of conductors with a different one of those conductors connected to ends of segments 22 and 23 at the fourth gap 26. The remote end of the coaxial cable is coupled to a transmitter/receiver (not shown) of the magnetic resonance imaging system, as conventional local coils are connected.

The area 29 of the sheet 16 within the RF coil 18 defines a surgical field through which the surgeon makes an incision 30 penetrating both the drape 14 and the patient's skin underneath the drape. The adhesive backing on the drape holds the coil in position about the incision for imaging the anatomical features being operated upon.

Although a circular RF coil 18 is illustrated, the coil may have other geometric shapes, such as oval squares or rectangles. In addition, although a single conductive loop type coil is used in the illustrated embodiment, multiple loop coils and other coil patterns can be incorporated into a surgical drape 14.

FIG. 3 illustrates a cross section through the RF coil 18 and drape 14. The sheet 16 is formed by two layers, a lower layer 31 having an exposed surface 33 on which the adhesive is applied to hold the drape in place on the skin of the patient 10. The coil 18 is attached to the opposite major surface of the first sheet 31 and comprises resilient foam material 34 that is curved in conformity with the circular shape of the coil 18. The flexible strips forming the conductive segments 21-24 are attached to the exposed surface of the foam material 34, such as by an adhesive. The lower layer 31 and foam material 34 electrically insulate the coil 18 from the patient's skin, preventing electric shock and burns.

The foam 34 and conductive segments 21-24 are covered by a layer 36 of a fabric, such as Kevlar or Kapton, which is resistant to penetration and cutting by conventional surgical instruments and needles. Fabric layer 36 protects the coil 18 from a surgical instrument severing the coil for altering the coil's electrical properties by penetration during the medical procedure. A second layer 32 of sheet 16 is applied over the first layer 31 covering the coil 18. The first and second layers 31 and 32 or adhered to one another providing an impervious seal around the coil 18 and coaxial cable 28. After fabrication, the two layers 31 and 32 are sterilized so that the drape 14 does not contaminate the operating environment.

During the operation, the backing layer of a waxed paper is removed from the surface 33 of the first sheet 31 exposing the adhesive. Surface 33 then is placed against the skin of the patient 10 and adhered thereto. The coaxial cable 28 is attached to the transmitter/receiver of the MRI system which is activated to produce images of the anatomy of the patient beneath the drape 14. The surgical procedure is performed on the patient 10 by making an incision 30 within the operating field defined by coil 18. The incision can be made utilizing non-magnetic instruments or a laser cutting device. During the procedure, the surgeon can observe the penetration of the instruments on the video monitor of the MRI system.

Upon completion of the surgery and closure of the incision, the drape is peeled from the skin of the patient and thrown away. The drape is a single use apparatus which does not lend itself to re-sterilization.

We claim:

1. A surgical drape for use during magnetic resonance imaging comprises:
    a sheet of sterile flexible material having a mechanism for adhering said sterile sheet to skin of a patient, and having an area through which an incision is made during an operation on the patient; and
    a flexible radio frequency coil tuned to a Larmor frequency of the magnetic resonance imaging and attached to said sterile sheet and surrounding the area.

2. The surgical drape as recited in claim 1 wherein said sheet of sterile flexible material comprises multiple layers bonded to each other with said radio frequency coil being sandwiched in between the layers.

3. The surgical drape as recited in claim 2 wherein an exposed surface of one of the layers has adhesive applied thereto for adhering said drape to the skin of the patient.

4. The surgical drape as recited in claim 2 wherein an exposed surface of one of the multiple layers has an adhesive applied thereto for adhering said drape to the skin of the patient; and further comprising a backing sheet applied to the exposed surface and said backing sheet has with a coating that allows the backing sheet to be removed without removing the adhesive from the exposed surface.

5. The surgical drape as recited in claim 2 wherein said flexible radio frequency coil comprises a foam material applied to a surface of one of the multiple layers; and a conductive element applied to a surface of the foam material.

6. The surgical drape as recited in claim 1 further including a layer of material that resists penetration by surgical instruments which layer covers said radio frequency coil for protection against accidental penetration.

7. A surgical drape for use during magnetic resonance imaging comprises:
    a sheet of sterile flexible material having a mechanism for adhering said sterile sheet to skin of a patient, and having an area through which an incision is made during an operation on the patient; and
    a flexible radio frequency coil tuned to a Larmor frequency of the magnetic resonance imaging and attached to said sterile sheet and surrounding the area, and wherein said flexible radio frequency coil comprises a plurality of segments forming a loop with a gap between ends of adjacent segments, a plurality of capacitors connected to ends of adjacent segments across the gaps, and a pair of conductors each attached to adjacent segments at one of the gaps.

8. A surgical drape for use during magnetic resonance imaging and intended to be disposed of after a single use, said surgical drape comprising:
    a first sheet of flexible material having first and second major surfaces with adhesive applied to the first major surface for adhering said first sheet to skin of a patient;
    a flexible radio frequency coil tuned to a Larmor frequency of magnetic resonance and applied to the second major surface of the first sheet and surrounding an area on the second major surface through which an incision is to be made during surgery on the patient;
    a layer of material that is resistant to penetration by surgical instruments covering exposed surfaces of said radio frequency coil for protection against accidental penetration; and
    a second sheet of flexible material bonded to said first sheet with said radio frequency coil being sandwiched in between the first and second sheets.

9. The surgical drape as recited in claim 8 wherein said flexible radio frequency coil comprises a foam material applied to the second major surface of said first sheet; and a conductive element applied to a surface of the foam material.

* * * * *